(12) United States Patent
Sanuki et al.

(10) Patent No.: US 7,323,693 B2
(45) Date of Patent: Jan. 29, 2008

(54) APPARATUS AND METHOD FOR MEASURING CURED STATE OF REACTION CURABLE RESIN

(75) Inventors: Tatsushi Sanuki, Kanagawa (JP); Naoko Miura, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 166 days.

(21) Appl. No.: 11/013,536

(22) Filed: Dec. 17, 2004

(65) Prior Publication Data

US 2005/0143483 A1 Jun. 30, 2005

(30) Foreign Application Priority Data

Dec. 25, 2003 (JP) ............................ 2003-430423
Nov. 18, 2004 (JP) ............................ 2004-334804

(51) Int. Cl.
*G01J 3/42* (2006.01)
(52) U.S. Cl. ..................................................... 250/372
(58) Field of Classification Search ................ 250/372
See application file for complete search history.

(56) References Cited

U.S. PATENT DOCUMENTS 4,624,971 A * 11/1986 van Tao et al. ............... 522/37

2002/0103439 A1 * 8/2002 Zeng et al. .................. 600/476
2003/0074095 A1 * 4/2003 Neubauer et al. ........... 700/117
2004/0036027 A1 * 2/2004 Horton et al. ............... 250/372

FOREIGN PATENT DOCUMENTS

JP 6-294734 10/1994
JP 2000-55806 2/2000

* cited by examiner

*Primary Examiner*—David Porta
*Assistant Examiner*—Shun Lee
(74) *Attorney, Agent, or Firm*—Fitzpatrick, Cella, Harper & Scinto

(57) ABSTRACT

A reaction curable resin is irradiated with ultraviolet light having wavelengths of 250 to 380 nm. A screen image of luminance value, which is obtained by extracting only a specific wavelength component of the reflected ultraviolet light, is recorded, and the cured state of an ultraviolet curable resin is quantified from a captured image and displayed. At the same time, the spectral characteristics of reflected light are measured by an ultraviolet spectroscope and a cured state is quantified in accordance with the change rate of absorbances obtained from a change of spectral characteristics by combining the spectral characteristic with a luminance value image and displayed.

8 Claims, 11 Drawing Sheets

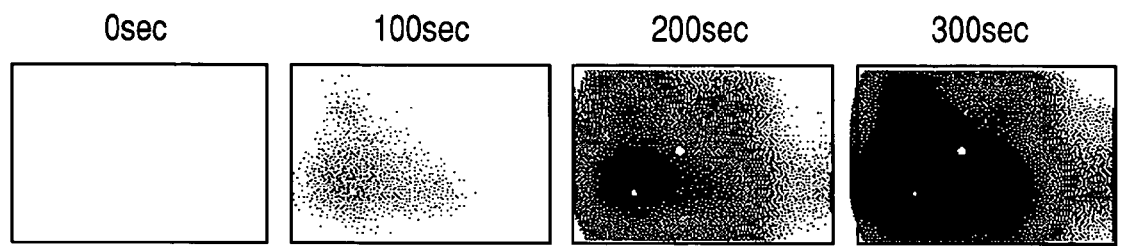
FIG. 8A 0sec  FIG. 8B 100sec  FIG. 8C 200sec  FIG. 8D 300sec
0%  REACTION RATE  100%
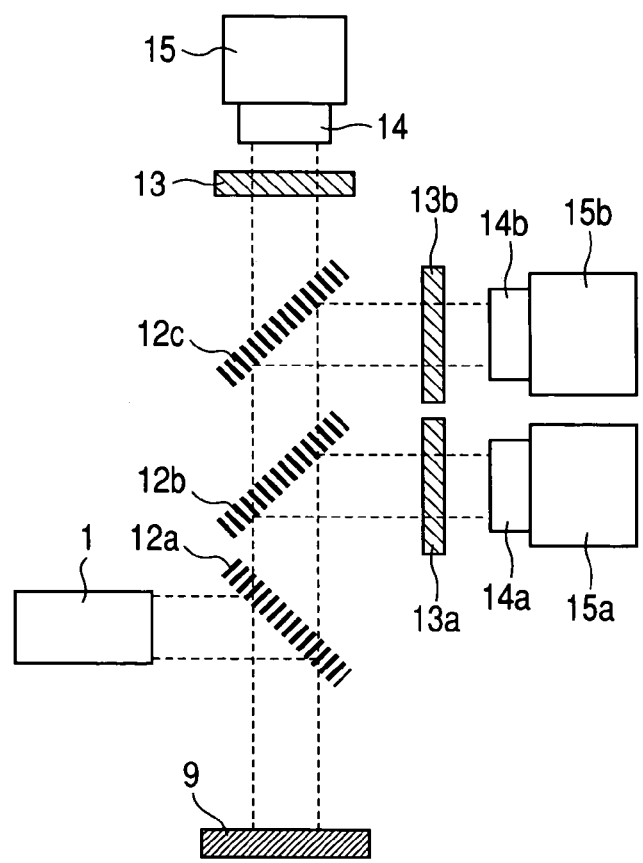
FIG. 9

APPARATUS AND METHOD FOR MEASURING CURED STATE OF REACTION CURABLE RESIN

BACKGROUND OF THE INVENTION

1. Field of the Invention

The present invention relates to an apparatus and a method for measuring a cured state of a reaction curable resin, which changes from liquid to solid by causing a chemical reaction when stimulated by light and heat. Particularly, the present invention relates to a measurement of a temporal change in the cured state.

2. Related Background Art

A reaction curable resin has been frequently used in fields of ink, paint, plastic-material coating and lens (glass lens). Particularly, it is known that a replica forming method using an ultraviolet curable resin is suitable as a process of forming an optical device having a miniature shape, such as a diffractive optical device.

In a replica formation method, an optical device is formed by dripping an ultraviolet curable resin on the previously polished lens surface to give the resin an aspherical shape using a mold and then applying ultraviolet radiation to cure a resultant aspherical layer, and releasing the molded item from the mold. However, the replica forming method, has a problem in that the resulting object may have a defective appearance due to the fluctuation in the cured state of an ultraviolet curable resin. Moreover, because curing excessively advances, the resin becomes more fragile and the optical device is chipped when it is released from the mold or, alternatively, the optical device having a desired shape cannot be obtained because it is released from the mold before being sufficiently cured. Therefore, determining optimum curing conditions by analyzing the cured state of the ultraviolet curable resin and identifying a factor causing the problem is very important.

As a method for analyzing and measuring a cured state of a reaction curable resin, infrared light spectrometry, such as FT-IR (Fourier transformation infrared spectral analysis), is generally used, as disclosed in Japanese Patent Application Laid-Open No. H06-294734. For measuring the cured state of a resin using FT-IR, it is known that any one of a photo-curing resin, heat curing resin and two-component system resin can be used. Moreover, to determine the temporal changes in the cured state of an ultraviolet curable resin, a method using an infrared spectrum peak is disclosed in Japanese Patent Application Laid-Open No. 2000-055806. The infrared spectrum peak detects changes in the molecular structures following the curing reaction of an ultraviolet curable resin and measures a change amount of peak intensities according to curing.

Generally, when curing a reaction curable resin, the whole resin is not uniformly cured. A distribution necessarily occurs in curing rates and there are irregularities in the cured states. Some of the factors that cause this distribution to occur include the following: a different position or angle of different portions of the resin to a light source or heat source, a difference in anaerobic characteristics of a resin due to a variance in the shape of the resin, resulting in different curing reaction rates in different portions of the surface of the resin, and the curing reaction rate in the interior portion of a resin differs from the outer portions, depending on the thickness of each portion of a resin. Therefore, a measuring method capable of measuring a change in cured states of the resin as a whole following the passage of time and displaying the change as a screen image is necessary.

However, the method using infrared spectroscopic analysis shown in Japanese Patent Application Laid-Open No. H06-294734 and the method using an infrared spectrum peak disclosed in Japanese Patent Application Laid-Open No. 2000-055806 are methods for respectively measuring the cured state at a single point in an object. Thus, it is impossible to use these methods to capture the cured state of the entire reaction curable resin as a screen image. In the case of these measuring methods using infrared light, the heat due to the infrared light propagates to a reaction curable resin. Therefore, in the case of a thermal curing resin whose curing reaction progresses due to heat, there is a problem in that the curing reaction of the resin is influenced by the heat and an accurate reaction state cannot be measured. Moreover, when measuring an optical device- produced by the replica forming method, a reaction curable resin is cured while it is held between a lens and a mold. Therefore, to measure the cured state of the reaction curable resin, it is necessary to measure the cured state through the lens. However, it is impossible to measure the cured state, because infrared light does not pass through the glass materials or plastic materials, which are used as the lens material.

SUMMARY OF THE INVENTION

It is an object of the present invention to make it possible to capture the cured state of a reaction curable resin as a screen image having a certain area, measure a cured state following a passage of time and evaluate and analyze the cured state as a quantitative value. Moreover, it is another object of the present invention to provide a cured-state measuring method and an apparatus capable of accurately measuring a cured state without generating heat that affects the curing during the measurement, even in the space surrounded by the glass or the like.

To solve the above problems, the present invention provides a reaction-curable-resin cured- state measuring apparatus including an ultraviolet light source for irradiating a reaction curable resin serving as an object to be measured with ultraviolet light, detection means for detecting ultraviolet light reflected from or transmitted through the reaction curable resin as screen image data having a certain area and image processing means for arithmetically processing the screen image data detected by the detection means and quantifying the progress of a curing reaction of the reaction curable resin following the passage of time as a screen image.

Moreover, the present invention provides a reaction-curable-resin cured-state measuring apparatus including an ultraviolet light source for irradiating a reaction curable resin serving as an object to be measured with ultraviolet light, a half mirror for branching the ultraviolet light reflected from or transmitted through the reaction curable resin in two directions, detection means for detecting one-hand ultraviolet light branched by the half mirror as screen image data having a certain area, an ultraviolet spectroscope for detecting the spectral characteristic at one specific point of the other-hand ultraviolet light branched of the half mirror and image processing means for arithmetic-processing the screen image data detected by the detection means and the spectral characteristic detected by the ultraviolet spectroscope and quantifying the progress of the curing reaction of the reaction curable resin following the passage of time as a screen image.

Furthermore, the present invention provides a reaction-curable-resin cured-state measuring method including a step of irradiating a reaction curable resin serving as an object to be measured with ultraviolet light, a step of detecting ultraviolet light reflected from or transmitted through the reaction curable resin as screen image data having a certain area, a step of arithmetically processing the detected screen image data and a step of quantifying the progress of a curing reaction of the reaction curable resin following the passage of time as a screen image.

Furthermore, the present invention provides a reaction-curable-resin cured-state measuring method in which the screen image data is detected by extracting only a light having a specific wavelength of reflected or transmitted ultraviolet light.

Furthermore, the present invention provides a reaction-curable-resin cured-state measuring method in which the screen image data is the luminance value of the reflected or transmitted ultraviolet light at least at one wavelength in a range of 250 to 380 nm and the wavelength is the one at which a change in luminance values following curing of the reaction curable resin appears as the largest value.

Furthermore, the present invention provides a reaction-curable-resin cured-state measuring method in which the quantified screen image is displayed by setting the change rate of the luminance values to 0% before the curing reaction and to 100% after the curing reaction, thereby displaying the change rate corresponding to the luminance values and changing colors at a plurality of gradations.

Furthermore, the present invention provides a reaction-curable-resin cured-state measuring method including a step of irradiating a reaction curable resin serving as an object to be measured with ultraviolet light, a step of branching ultraviolet light reflected or transmitted from the reaction curable resin in two directions, a step of detecting branched one-hand ultraviolet light as screen image data having a certain area, a step of detecting the spectral characteristic of the other branched ultraviolet light at one specific point, and a step of arithmetically processing the detected screen image data and spectral characteristic and quantifying the progress of a curing reaction of the reaction curable resin following the passage of time as a screen image.

Furthermore, the present invention provides a reaction-curable-resin cured-state measuring method in which the screen image data is a luminance value of the reflected or transmitted ultraviolet light at least at one wavelength in a range of 250 to 380 nm and the wavelength is the one at which a change in luminance values following curing of the reaction curable resin appears as the largest value.

Furthermore, the present invention provides a reaction-curable-resin cured-state measuring method in which the quantified screen image is displayed by converting the luminance value into an absorbance obtained from the spectral characteristic, setting the change rate of the absorbance to 0% before the curing reaction and to 100% after the curing reaction, and displaying the change rate of the absorbance changing colors at a plurality of gradations.

Furthermore, the present invention provides a reaction-curable-resin cured-state measuring method in which the reaction curable resin is an ultraviolet curable resin.

Furthermore, the present invention provides a reaction-curable-resin cured-state measuring method in which the reaction curable resin is an ultraviolet curable resin for forming an optical device through replica molding.

The above and other objects of the invention will become more apparent from the following description taken in conjunction with the accompanying drawings.

BRIEF DESCRIPTION OF THE DRAWINGS

FIGS. 8A, 8B, 8C and 8D are images obtained by measuring cured states of the resin in Embodiment 2;

FIG. 9 is a schematic view of a resin-cured-state measuring apparatus Embodiment 3;

DESCRIPTION OF THE PREFERRED EMBODIMENTS

Embodiments of the present invention are described below by referring to the accompanying drawings.

Embodiment 1

Figure 1:
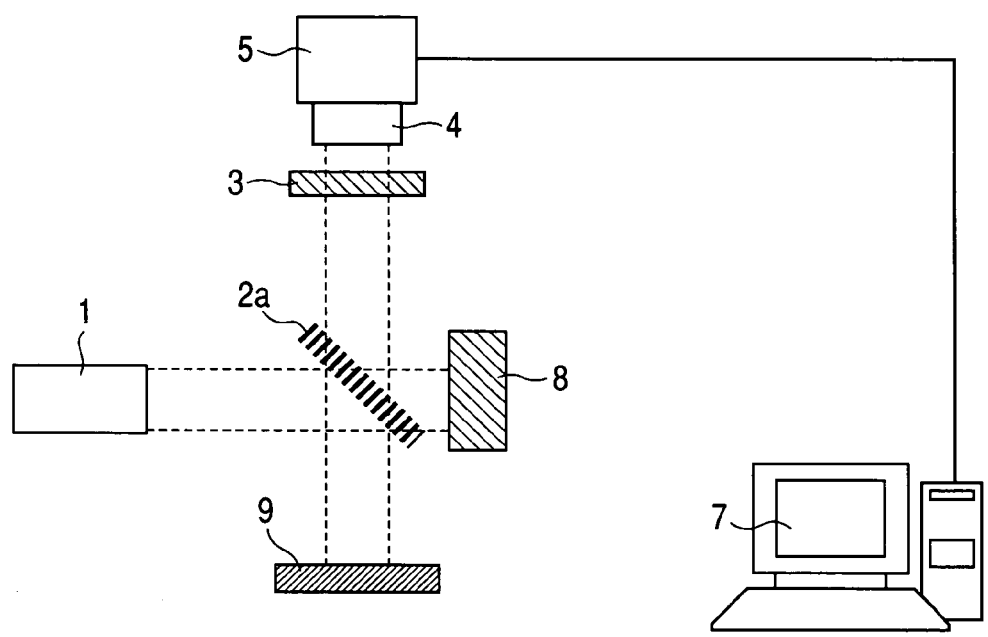
FIG. 1 is a schematic view of a resin-cured-state measuring apparatus in Embodiment 1.

FIG. 1 is a schematic view showing the reaction-curable-resin cured-state measuring apparatus in Embodiment 1 of the present invention. In this case, an ultraviolet curable resin is used as a reaction curable resin. This embodiment may be used to quantify and display the cured state of an ultraviolet curable resin by irradiating it with ultraviolet light and measuring the reflected light.

In FIG. 1, reference numeral 9 denotes an object to be measured (measuring object) made of an ultraviolet curable resin. Reference numeral 1 denotes an ultraviolet light source. Reference numeral 2a denotes a half mirror for branching the ultraviolet light emitted from the ultraviolet light source 1 in two directions. Reference numeral 3 denotes a band-pass filter for passing only a specific wavelength component of ultraviolet light. Reference numeral 4 denotes an ultraviolet lens capable of condensing ultraviolet light and reference numeral 5 denotes an ultraviolet CCD camera for picking up as a screen image ultraviolet light reflected from a measuring object and condensed by the ultraviolet lens 4. By changing specifications of the ultraviolet CCD camera 5 and the band-pass filter 3, it is possible to change the wavelength of the ultraviolet light to be measured to an optimum value for showing better a change in cured states. Reference numeral 7 denotes an image processing apparatus for storing the luminance value of a measuring object made of an ultraviolet curable resin, converting the luminance value into a cured state and displaying the cured state. The image processing apparatus 7 quantifies the cured state of the measuring object 9 from a change in luminance values obtained from the ultraviolet CCD camera 5 and displays the cured state. Reference numeral 8 denotes a stray-light removal plate to shield unnecessary ultraviolet light.

In the case of acrylic resins and epoxy resins widely used as ultraviolet curable resins, the intensity of ultraviolet light to be transmitted gradually becomes weak as curing progresses in an ultraviolet wavelength band. That is, the luminance value of the light reflected from an ultraviolet curable resin is changed in accordance with the progress of the curing reaction of the ultraviolet curable resin. This embodiment quantifies a cured state from a change in luminance values of the light reflected from an ultraviolet curable resin and displays the cured state.

The ultraviolet light (wavelengths of 250 to 380 nm) emitted from the ultraviolet light source 1 is first divided into two directions, such as direct advance and reflection, by a half mirror 2a. The direct-advance ultraviolet light is shielded by the stray-light removal plate 8. The ultraviolet light reflected from the half mirror 2a irradiates an ultraviolet curable resin serving as an object to be measured. The curing reaction of the ultraviolet curable resin is slowly progresses due to the ultraviolet light. only a specific wavelength component is extracted from the ultraviolet light reflected from the ultraviolet curable resin by the band-pass filter 3 and is picked up as a screen image by the ultraviolet CCD camera 5. The image picked up by the ultraviolet CCD camera 5 is sent to the image processing apparatus 7. The image processing apparatus 7 converts the image data picked up by the ultraviolet CCD camera 5 into luminance value data and stores the data. After curing of the ultraviolet curable resin is completed, the apparatus 7 processes the stored luminance value data, quantifies the processed data so as to display a change of cured states of the ultraviolet curable resin and displays the data as a screen image.

Now, a method will be described in detail, which method quantifies the cured states of an ultraviolet curable resin from a change in luminance values in each cured state captured by the image processing apparatus 7 and displays the result. It is assumed that the image luminance value at the start of curing, that is, at a reaction rate of 0%, is 0, and the image luminance value when curing is completed, that is, at a reaction rate of 100%, is 256. It is assumed that a change in image luminance values at this time is changed proportionally to a measured luminance value. The image luminance value at each position of the ultraviolet curable resin is obtained from the image luminance value and displayed at 256 gradations.

Figures 2A, 2B, 2C, 2D:
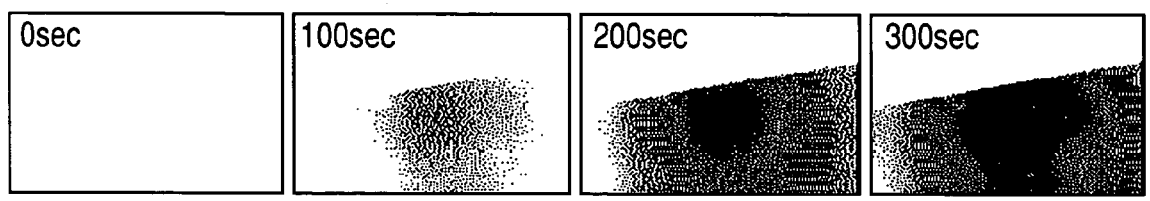
FIGS. 2A, 2B, 2C and 2D are images obtained by measuring cured states of the resin in Embodiment 1.

FIGS. 2A to 2D are screen images of a change of luminance values following curing of a general epoxy ultraviolet curable resin obtained from the CCD camera 5. In the case of the ultraviolet light obtained by the CCD camera 5, only a wavelength of 350 nm at which curing of the epoxy ultraviolet curable resin progresses at the highest speed is selected by the band-pass filter 3. FIG. 2A shows as an image the luminance value 0 of an ultraviolet curable resin before curing is initiated. FIG. 2B shows as an image the luminance value of the ultraviolet curable resin 100 sec after curing was initiated. FIG. 2C shows as an image the luminance value of the ultraviolet curable resin 200 sec after curing was initiated. FIG. 2D shows as an image the luminance value of the ultraviolet curable resin 300 sec after curing was initiated. As shown in FIGS. 2A to 2D, it was found that the image luminance value of the ultraviolet curable resin gradually decreases with the passage of time and the curing reaction progresses.

This embodiment makes it possible to measure the cured state of an ultraviolet curable resin in accordance with irradiation not of infrared or visible light, which generate heat, but of ultraviolet light. Moreover, it is possible to capture a change in the cured states of an ultraviolet curable resin as a screen image and display the change of the cured states following a passage of time.

Embodiment 2

The ultraviolet-curable-resin cured-state measuring method shown in Embodiment 1 can display a change in the cured states of an ultraviolet curable resin as a screen image. The present inventors discovered that an even more clear screen image can be displayed by showing a temporal change of the cured states of an ultraviolet curable resin in terms of a change rate in absorbance obtained from the spectral characteristics of the light reflected from the ultraviolet curable resin.

In this case, the relationship between the change rate of the absorbances from which spectral characteristics can be obtained when applying ultraviolet light to an ultraviolet curable resin and the reaction rate obtained from an infrared spectrum change measured by the FT-IR disclosed in Japanese Patent Application Laid-Open No. H06-294734 is described below. The reaction rate of an ultraviolet curable resin obtained from an infrared spectrum change is known for very clearly showing a cured state. In this case, the ultraviolet curable resin containing an acrylic monomer (trade name GRANDIC RC C001 made by DAINIPPON INK AND CHEMICALS, INC.) (hereafter referred to as C001) is used as an example and a change rate of the absorbances in the ultraviolet radiation region and a reaction rate obtained from an infrared spectral change are compared and described below.

Figure 3:
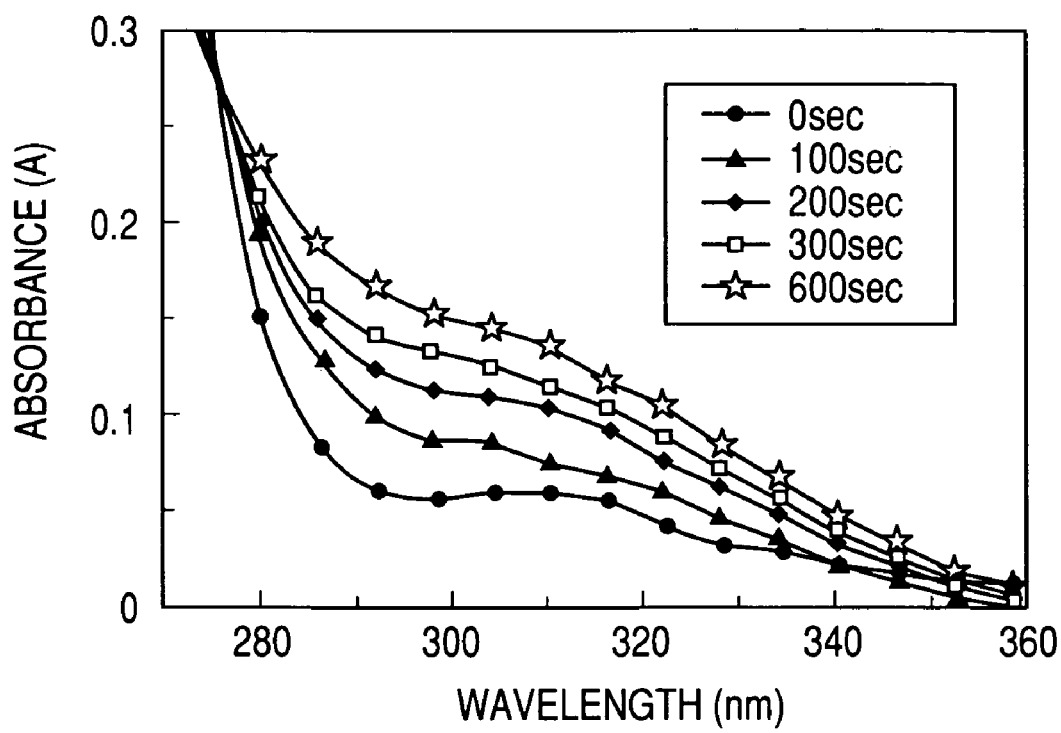
FIG. 3 is a plot with graphs showing the states of absorbance changes following ultraviolet irradiation of ultraviolet curable resin C001.

FIG. 3 shows a state of absorbance changes at the light wavelength of the ultraviolet curable resin C001 measured by an ultraviolet spectroscope. Moreover, FIG. 3 shows absorbance changes at 0 sec, 100 sec, 200 sec, 300 sec and 600 sec from start of curing. FIG. 3 shows that the ultraviolet curable resin C001 is almost transparent in a visible light region at a wavelength of 380 nm or more and an absorbance change following curing is not seen. However, the absorbance changes in an ultraviolet wavelength band at 250 to 380 nm. Moreover, it is found that the absorbance of the resin C001 substantially increases at an ultraviolet wavelength of approx. 300 nm as a curing reaction progresses.

Figure 4:
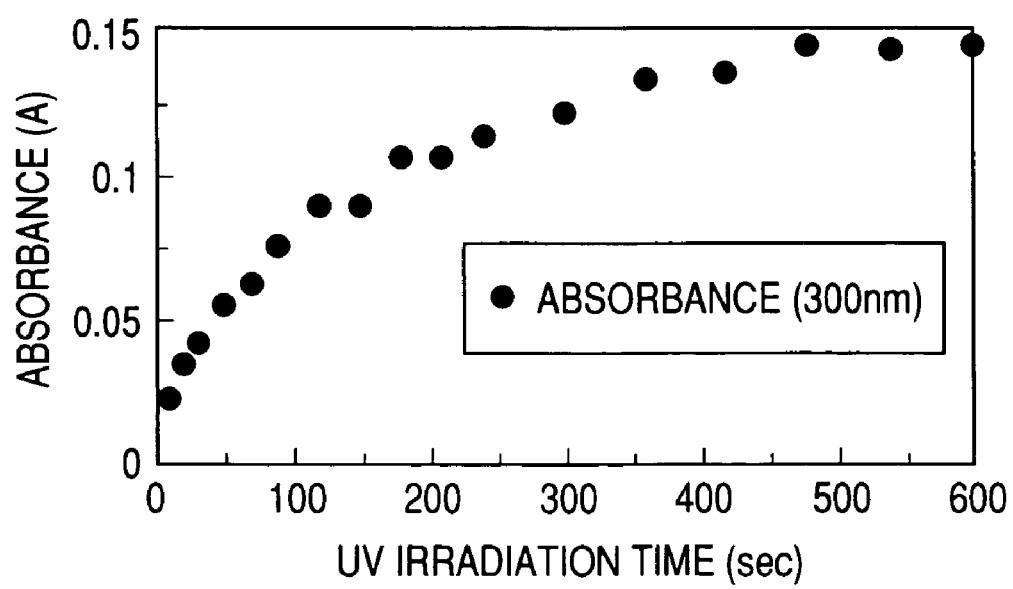
FIG. 4 is a graph showing the state of an absorbance change at a wavelength of 300 nm following ultraviolet irradiation of the ultraviolet curable resin C001.

FIG. 4 shows a temporal change in absorbance at a wavelength of 300 nm of the ultraviolet curable resin C001 shown in FIG. 3. It is found that the absorbance exponentially increases simultaneously with the start of curing and then becomes almost constant after reaching the maximum value for approximately 500 sec. In this case, the absorbance difference between the time before curing and the time of completion of curing is 0.15 and this value is large enough for measuring an image.

Figure 5:
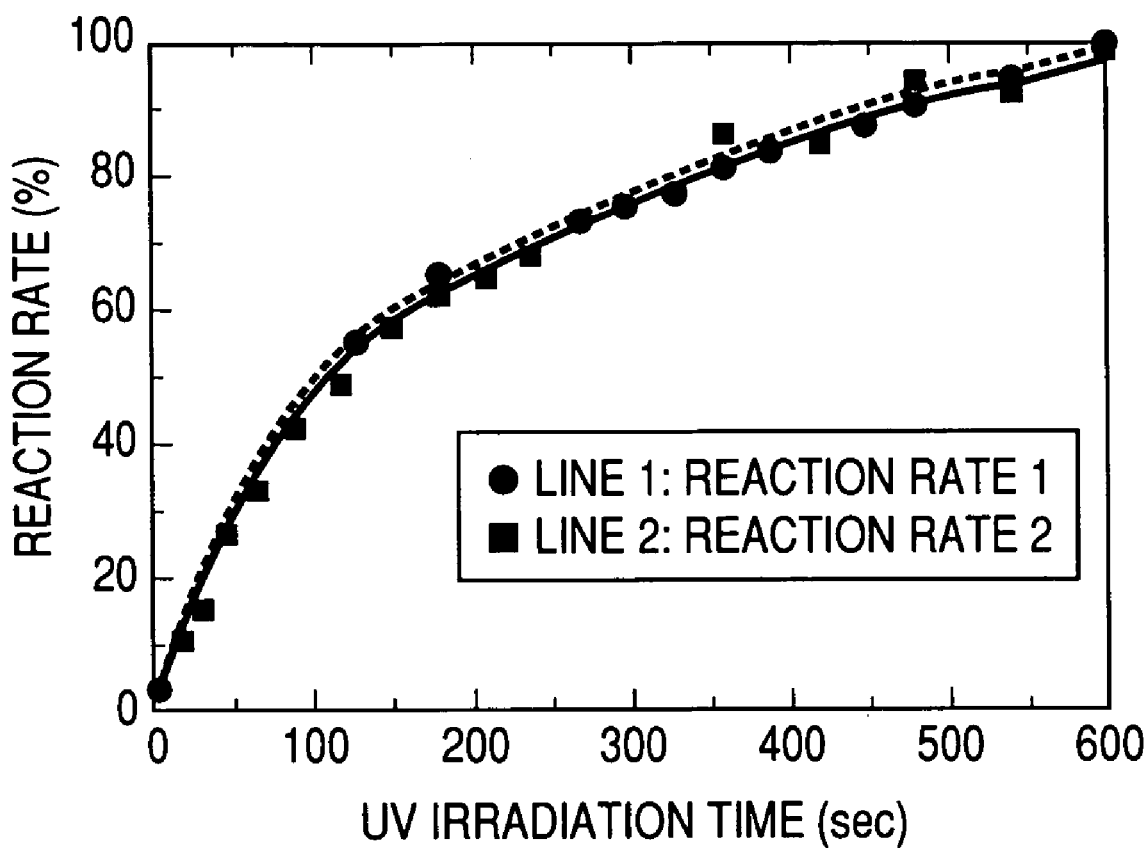
FIG. 5 is a plot with graphs showing a reaction rate 1 calculated from the infrared spectrum of the ultraviolet curable resin C001 and a reaction rate 2 calculated from the change rate of the image luminance value of the ultraviolet curable resin.

When showing a change rate of absorbances following the passage of time, obtained from the absorbances shown in FIG. 4, as a reaction rate assuming it is 0% when curing is initiated and 100% when curing is completed, the line 1 (reaction rate 1) shown by a continuous line in FIG. 5, is obtained. Moreover, when measuring the infrared spectrum of the ultraviolet curable resin C001 by FT-IR, the reaction rate is obtained as dotted line 2 (reaction rate 2), shown in FIG. 5. The reaction rate 2 can be obtained by the following (Expression 1) and (Expression 2).

X={(Absorbance 1/Absorbance 2)/(Absorbance 3/Absorbance 4)}×100   (Expression 1)

X: Remaining rate of double bonds of carbon

Reaction rate (%)=100−X   (Expression 2)

In this case, because the molecular structure of the ultraviolet curable resin C001 has carbon double bonds, the ultraviolet curable resin C001 has the absorption peak at a wavelength of 810 cm$^{-1}$ (12.3 μm). The absorbance 1 is at a wavelength of 12.3 μm at a certain time after curing is started and the absorbance 3 is at a wavelength of 12.3 μm before curing is started.

Moreover, because the ultraviolet curable resin C001 has a benzene ring in its molecular structure, it also has the absorption peak at a wavelength of 756 cm$^{-1}$ (13.2 μm). The absorbance 2 is at the wavelength of 13.2 μm at a certain time after curing is started and the absorbance 4 is at a wavelength of 13.2 μm before curing is started.

The ultraviolet curable resin C001 is polymerized, because double bonds in the carbon are ring-opened as curing progresses. The value of the absorbance 1 gradually decreases as curing progresses. However, even if curing progresses, the value of the absorbance 2 is not changed, because the structure of the benzene ring is not influenced. Therefore, as shown in Expression 1, as a result of tracing the temporal change after irradiation of ultraviolet light of the ratio between the absorbances 1 and 2 of the ultraviolet curable resin C001 and the ratio between the absorbances 3 and 4 of the resin C001 before starting the curing process, the carbon-double-bond remaining rate (X) showing how many carbon double bonds are no longer present due to curing is known. The reaction rate of the ultraviolet curable resin C001 can be obtained from the value of X obtained through Expression 1 by Expression 2.

In FIG. 5, the reaction rate of the line 1 coincides with that of the line 2 very well. Therefore, the reaction rate 2 obtained from using an infrared spectrum can be replaced with the change rate 1 obtained from the absorbance measured by an ultraviolet spectroscope using ultraviolet light. That is, the cured state of an ultraviolet curable resin can be accurately obtained in such a manner that the cured state of the ultraviolet curable resin measured by irradiation of ultraviolet light is quantified to a value equivalent to the reaction rate of an infrared spectrum, which is known to show very clearly a cured state.

Figure 6:
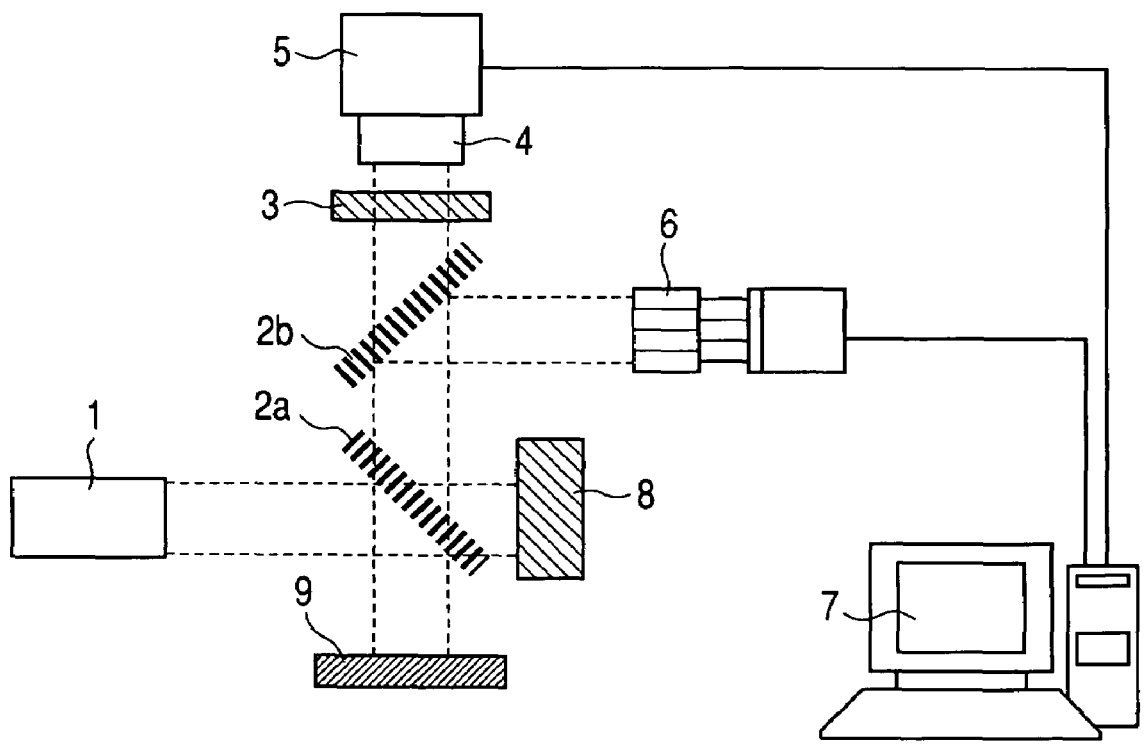
FIG. 6 is a schematic view of a resin-cured-state measuring apparatus in Embodiment 2.

FIG. 6 is a schematic view showing a reaction-curable-resin cured-state measuring apparatus used in the embodiment 2 of the present invention. In this case, an ultraviolet curable resin is used as a reaction curable resin. This embodiment quantifies the cured state of the ultraviolet curable resin by a change rate in absorbance obtained from a change in spectral characteristics and displays the quantified cured state by irradiating the ultraviolet curable resin with ultraviolet light and measuring the reflected light. In this Embodiment, members that are the same as those in Embodiment 1 are labeled by the same reference numerals.

In FIG. 6, reference numeral 9 denotes an object to be measured (measuring object) made of an ultraviolet curable resin. Reference numeral 1 denotes an ultraviolet light source. Reference numerals 2a and 2b denote half mirrors for branching the ultraviolet light emitted from the light source 1 in two directions. Reference numeral 3 denotes a band-pass filter for passing only a specific wavelength component of ultraviolet light. Reference numeral 4 denotes an ultraviolet lens capable of condensing ultraviolet light and 5 denotes an ultraviolet CCD camera for picking up the ultraviolet light reflected from a measuring object condensed by the ultraviolet lens 4 as screen image data. Reference numeral 6 denotes a compact ultraviolet spectroscope for measuring the wavelength and intensity (spectral characteristics) at a certain one point of the ultraviolet light reflected from a measuring object. The compact ultraviolet spectroscope cannot capture the light reflected from the measuring object as a screen image or it can measure only the wavelength and intensity (spectral characteristics) at a certain one point. Reference numeral 7 denotes an image processing apparatus for converting the luminance value of a measuring object made of an ultraviolet curable resin into a cured state and displaying the cured state. The image processing apparatus 7 quantifies the cured state of the measuring object 9 from the change in luminance values obtained from the ultraviolet CCD camera 5 and the spectral characteristics obtained from the compact ultraviolet spectroscope 6 and displays the cured state. Reference numeral 8 denotes a stray light removal plate for shielding unnecessary ultraviolet light.

In the case of each of acrylic resins and epoxy resins, which are widely used as ultraviolet curable resins, the luminance value of reflected ultraviolet light changes due to the curing reaction of each ultraviolet curable resin in the ultraviolet wavelength band as described above. In this case, it can be known at what time the ultraviolet curable resin changes its resin structure to a chemical structure for absorbing ultraviolet wavelength light. That is, when the molecular structure of the ultraviolet curable resin changes, the spectral characteristic of the ultraviolet curable resin also changes. The embodiment quantifies the cured state of an ultraviolet curable resin from a screen image picked up by the CCD camera 5 and taken in to the image processing apparatus 7 and a value picked up by the compact ultraviolet spectroscope 6 and displays the quantified cured state.

First, the ultraviolet light (wavelengths of 250 to 380 nm) emitted from the ultraviolet light source 1 is divided into two directions of direct advance and reflection by the half mirror 2a. The direct-advance ultraviolet light is shielded by the stray light removal plate 8. The ultraviolet light reflected from the half mirror 2a is applied to an ultraviolet curable resin serving as an object to be measured. The curing reaction of the ultraviolet curable resin is gradually progressed by ultraviolet light. The ultraviolet light reflected from the ultraviolet curable resin passes through the half mirror 2a and is divided into two directions of direct advance and reflection again by the half mirror 2b. Only a specific wavelength component is extracted from the ultraviolet light passing through the half mirror 2b by a band-pass filter 3 and picked up as a screen image by the ultraviolet CCD camera 5. The image picked up by the ultraviolet CCD camera 5 is sent to the image processing apparatus 7. Moreover, the intensity information of the ultraviolet light reflected from the half mirror 2b is measured by the compact ultraviolet spectroscope 6, and the measured value is sent to the image processing apparatus 7. The image processing apparatus 7 converts the image picked up by the ultraviolet CCD camera 5 into luminance value data and stores the data. Moreover, the apparatus 7 converts the value picked up by the compact ultraviolet spectroscope 6 into absorbance data and stores the data. After curing of the ultraviolet curable resin is completed, the apparatus 7 quantifies the changes in the cured state of the ultraviolet curable resin by comparing and combining the stored luminance value data and absorbance data and displays the changes.

Then, a method for quantifying the cured state of an ultraviolet curable resin from the screen image data picked up by the CCD camera 5 and taken in by the image processing apparatus 7 and the value picked up by the compact ultraviolet spectroscope 6 is described below.

Figure 7:
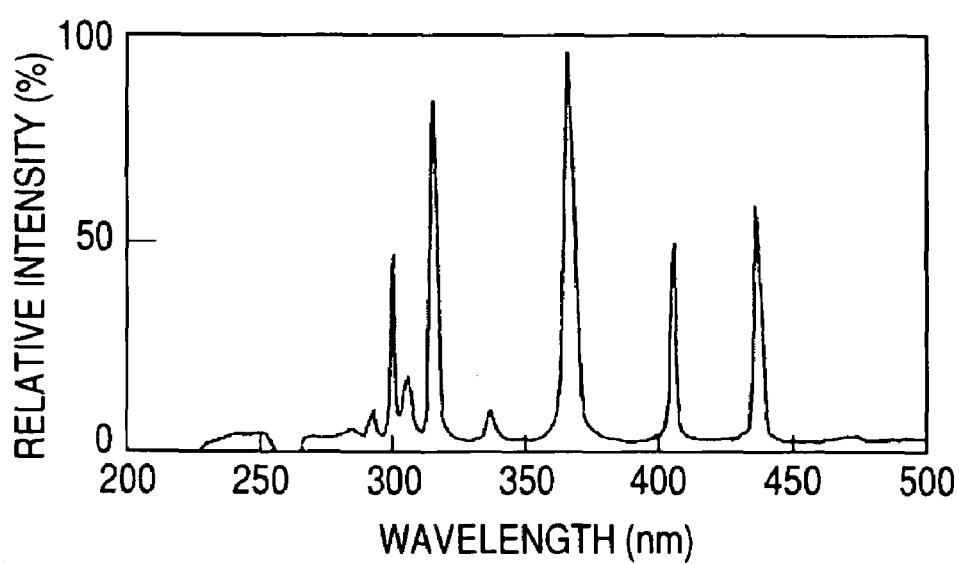
FIG. 7 is a graph showing the spectrum of an ultraviolet light source for measurement.

First, the screen image picked up by the CCD camera 5 is the same as that in Embodiment 1. The luminance value in each cured state is successively stored in the image processing apparatus 7 in accordance with the progress of the curing reaction. At the same time, the spectral characteristics at a desired point of the ultraviolet curable resin are measured by the compact ultraviolet spectroscope 6 to obtain the absorbance. The absorbance value in each cured state is also successively stored in accordance with the progress of a curing reaction. The ultraviolet light emitted from the ultraviolet light source 1 has a broad intensity at wavelengths of 250 to 380 nm, as shown in FIG. 7. The absorbance ($\alpha$) in this case can be obtained from the following expression (3).

Absorbance ($\alpha$)=$-\log(I/I_0)$    (Expression 3)

I: Intensity of UV light passing through a cured sample; and $I_0$: Intensity of UV light entering the sample.

As a curing reaction progresses, the intensity I of the light passing through an ultraviolet curable resin gradually decreases compared to the intensity $I_0$ of the light entering the sample. Therefore, the absorbance ($\alpha$) gradually increases as the curing reaction progresses. Incidentally, the intensity Io of the light entering the sample is assumed to be a constant value. In this case, the absorbance ($\alpha$) of the ultraviolet curable resin being cured is stored until curing of the ultraviolet curable resin is completed while relating it with the luminance value picked up by the CCD camera 5.

Then, after curing of the ultraviolet curable resin is completed, the luminance value picked up by the CCD camera 5 and the absorbance obtained from the compact ultraviolet spectroscope 6 are arithmetically processed. First, the luminance value in each cured state of the ultraviolet curable resin as picked up by the CCD camera 5 is converted into the absorbance obtained from the compact ultraviolet spectroscope 6. Then, the change rate of the absorbances at each position of the ultraviolet curable resin is obtained by assuming the luminance value at the start of curing, that is, at a reaction rate of 0% as 0 and the luminance value at the completion of curing, that is, at a reaction rate of 100% as 256, to display the change rate in 256 gradations.

Then, a method for quantifying the cured state of an ultraviolet curable resin from a change in luminance values in each cured state captured by the image processing apparatus 7 and for displaying the cured state is described below in detail. FIGS. 8A to 8D show image luminance values of an epoxy ultraviolet curable resin of Embodiment 1 shown in FIG. 2 as being replaced with absorbance change rates. FIG. 8A shows the change rate at the surface of an ultraviolet curable resin before curing is started, as an image. FIG. 8B shows the change rate of the ultraviolet curable resin 100 sec after starting the curing process, as an image. FIG. 8C shows the change rate of the ultraviolet curable resin 200 sec after starting the curing process, as an image. FIG. 8D shows the change rate of the ultraviolet curable resin 300 sec after starting the curing process, as an image. From FIGS. 8A to 8D, it is found that in the case of the ultraviolet curable resin, the curing reaction successively progresses with the passage of time.

Moreover, the change in the cured states of the ultraviolet curable resin can be more clearly seen in FIGS. 8A to 8D than in FIG. 2 in Embodiment 1. That is, according to Embodiment 2, it is possible to more accurately measure the cured state of an ultraviolet curable resin by applying ultraviolet light. Moreover, it is possible to capture a change in the cured states of an ultraviolet curable resin as a clearer screen image and more accurately display the change following the passage of time.

Furthermore, in this Embodiment 2, a luminance value picked up by the CCD camera 5 and a spectral characteristic measured by the compact ultraviolet spectroscope 6 are stored until curing of an ultraviolet curable resin is completed, and then, an arithmetical operation of these values is performed. However, the present invention makes it possible to perform an arithmetical operation simultaneously with measurement of an ultraviolet curable resin and display a cured state in real time by measuring the spectral characteristics of the ultraviolet curable resin before a curing reaction and after completion of the curing reaction.

Embodiment 3

FIG. 9 is a schematic view showing a reaction-curable-resin cured-state measuring apparatus used in Embodiment 3 of the present invention. As shown in FIG. 9, by continuously arranging a plurality of dichroic mirrors, it is possible to measure rays of a plurality of wavelengths at the same time.

In FIG. 9, reference numeral 1 denotes an ultraviolet light source and 9 denotes an object to be measured made of an ultraviolet curable resin. Reference numerals 12a, 12b and 12c denote dichroic mirrors for reflecting only a certain wavelength and passing rays of other wavelengths and 13a, 13b and 13 denote band-pass filters. Reference numerals 14a and 14b denote ultraviolet lenses and 15a and 15b denote ultraviolet CCD cameras. Reference numeral 14 denotes a visible light lens and 15 denotes a visible-light CCD camera. According to this embodiment, it is also possible to carry out the measurement at wavelengths including not only ultraviolet light, but also visible light using the spectral characteristics of any one of the dichroic mirrors 12a, 12b and 12c corresponding to a wavelength to be measured.

For example, it is also possible to measure ultraviolet light of 300 nm by the dichroic mirror 12a, band-pass filter 13a, ultraviolet lens 14a and ultraviolet CCD camera 15a, ultraviolet light of 350 nm by the dichroic mirror 12b, band-pass filter 13b, ultraviolet lens 14b and ultraviolet CCD camera 15b and visible light of 500 nm by the dichroic mirror 12c, band-pass filter 13, visible light lens 14 and visible light CCD camera 15.

Embodiment 4

Figure 10:
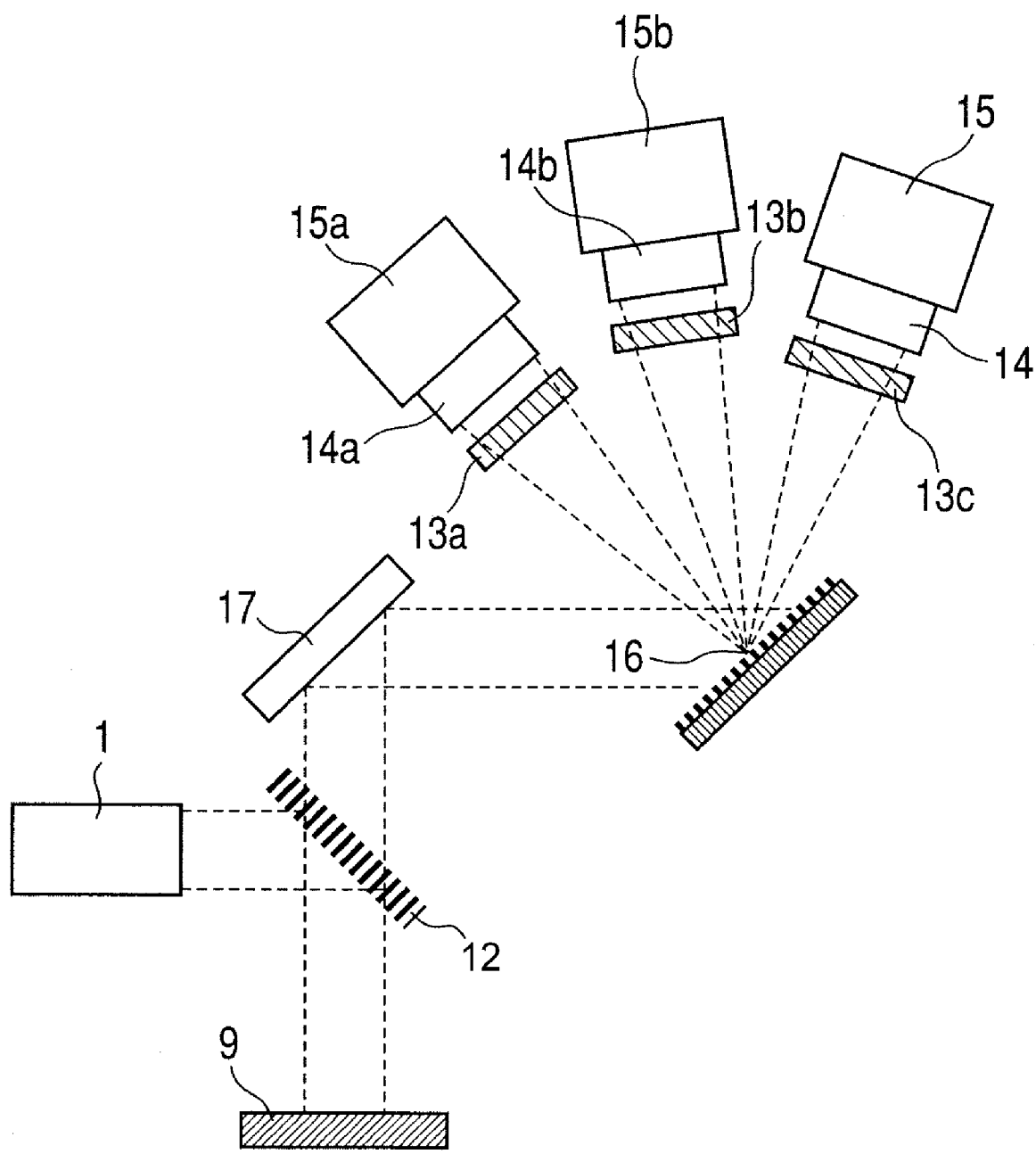
FIG. 10 is a schematic view of a resin-cured-state measuring apparatus in Embodiment 4.

FIG. 10 is a schematic view showing a reaction-curable-resin cured-state measuring apparatus of Embodiment 4 of the present invention. In this Embodiment, a diffraction grating 16 is set in which light of a specific wavelength is reflected in a specific direction. By capturing the light reflected from the diffraction grating 16 by a plurality of optical systems respectively constituted of an ultraviolet lens and an ultraviolet CCD corresponding to each wavelength, it is possible to measure rays of a plurality of wavelengths at the same time.

In FIG. 10, reference numeral 1 denotes an ultraviolet light source and 9 denotes an object to be measured made of an ultraviolet curable resin. Reference numeral 12 denotes a dichroic mirror for reflecting only a certain wavelength and passing rays of other wavelengths and 17 denotes a reflection mirror. Reference numerals 13a, 13b and 13c denote band-pass filters. Reference numerals 14a and 14b denote ultraviolet lenses and 15a and 15b denote ultraviolet CCD cameras. Reference numeral 14 denotes a visible light lens and 15 denotes a visible-light CCD camera. Reference numeral 16 denotes a diffraction grating capable of performing a measurement not only in the ultraviolet light region, but also at wavelengths up to the visible light region by using a grating capable of diffracting the light of a wavelength to be measured. That is, by using the spectral characteristic of any one of the dichroic mirrors 12a, 12b and 12c corresponding to a wavelength to be measured, it is possible to perform the measurement not only in the ultraviolet light region, but also at wavelengths up to the visible light region.

For example, it is also possible to measure the ultraviolet light of 300 nm by the diffraction grating 16, band-pass filter 13a, ultraviolet lens 14a and ultraviolet CCD camera 15a, the ultraviolet light of 350 nm by the diffraction grating 16, band-pass filter 13b, ultraviolet lens 14b and ultraviolet CCD camera 15b and the visible light of 500 nm by the diffraction grating 16, band-pass filter 13c, visible-light lens 14 and visible-light CCD camera 15.

Embodiment 5

Figure 11:
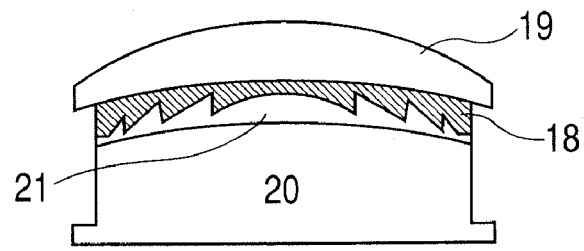
FIG. 11 is a sectional view of a diffractive optical device to be measured in Embodiment 5.

FIG. 11 is a sectional view showing the state in which a diffraction optical device serving as an object to be measured in Embodiment 5 of the present invention is held between a molding die and a base material. In FIG. 11, reference numeral 18 denotes an ultraviolet curable resin C001 to be cured by ultraviolet light. Reference numeral 19 denotes a glass base material serving as a diffraction optical device by being joined with the ultraviolet curable resin 18. Reference numeral 20 denotes a molding die for forming the shape of the ultraviolet curable resin 18 and a minute shape 21 for transferring the shape to the diffraction optical device is formed on the surface of the molding die.

Figure 12:
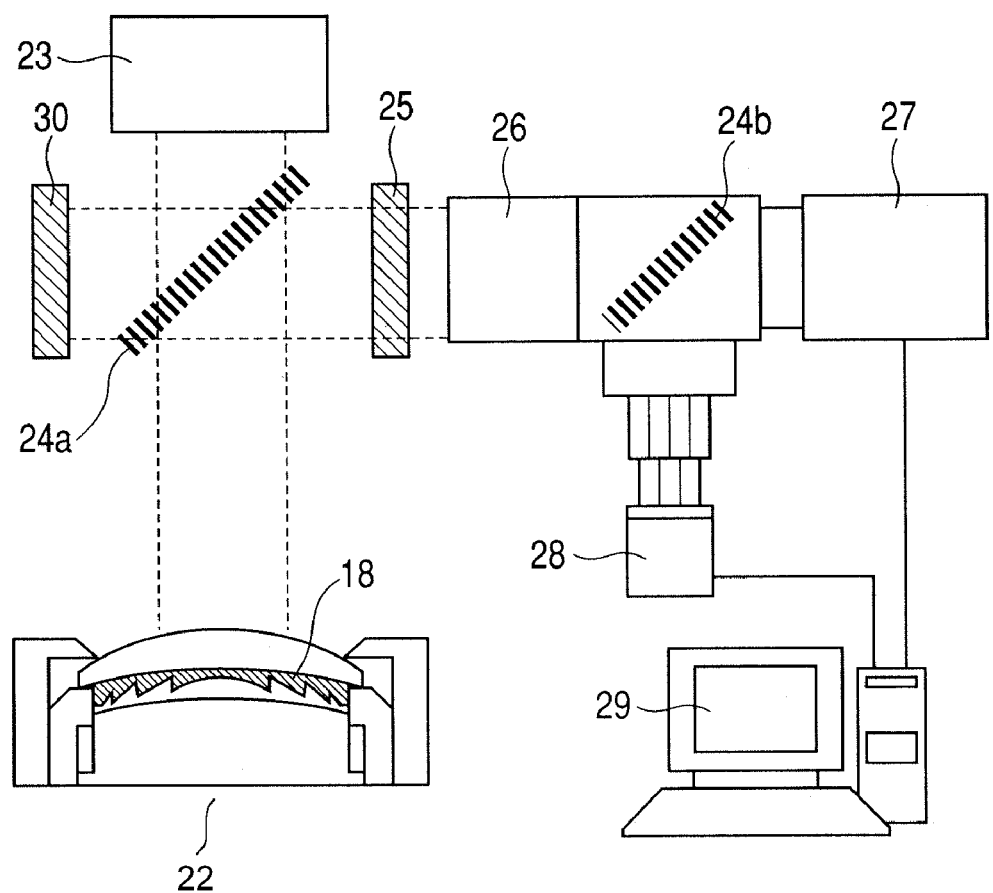
FIG. 12 is an schematic view of a measurement being conducted in Embodiment 5.

FIG. 12 is a schematic view showing a reaction-curable-resin cured-state measuring apparatus. The configuration of the measuring apparatus in FIG. 12 is principally the same as that of the measuring apparatus in FIG. 6, but its arrangement is different. In FIG. 12, reference numeral 22 denotes an object to be measured (measuring object) in which the ultraviolet curable resin 18 is held between the glass base material 19 and the molding die 20, as shown in FIG. 11. Reference numeral 23 denotes an ultraviolet light source. Reference numeral 24a denotes a half mirror for branching the ultraviolet light emitted from the light source 1 in two directions. Reference numeral 25 denotes a band-pass filter for passing only a specific wavelength component of ultraviolet light. Reference numeral 26 denotes an ultraviolet lens capable of condensing ultraviolet light. Reference numeral 27 denotes an ultraviolet CCD camera for picking up, as a screen image, the ultraviolet light reflected from a measuring object and condensed by the ultraviolet lens 26. Reference numeral 24b denotes a half mirror for branching the ultraviolet light passing through the ultraviolet lens 26 in two directions. Reference numeral 28 denotes a compact ultraviolet spectroscope for measuring the wavelength and intensity (spectral characteristics) of the ultraviolet light branched by the half mirror 24b. Reference numeral 29 denotes an image processing apparatus for converting the luminance value of a measuring object made of an ultraviolet curable resin into a cured state and displaying the cured state. Reference numeral 30 denotes a stray light removal plate for shielding unnecessary ultraviolet light.

The ultraviolet light (wavelengths of 250 to 380 nm) emitted from the ultraviolet light source 23 is divided into two directions of direct advance and reflection by the half mirror 24a. The half mirror 24a reflects the light having wavelengths of 250 to 380 nm by 50% and passes the light by 50%. The direct-advance ultraviolet light is shielded by the stray light removal plate 30. The ultraviolet curable resin 18 serving as a measuring object is irradiated with the ultraviolet light reflected from the half mirror 24a. The curing reaction of the ultraviolet curable resin 18 is gradually progressed by the ultraviolet light. The absorbance of the ultraviolet curable resin 18 is changed at the above-described ultraviolet wavelength band in accordance with the curing reaction. The ultraviolet light passing through the ultraviolet curable resin 18 and reflected from the surface of the molding die 20 is then reflected by the half mirror 24a, and only the ultraviolet light having a wavelength of 300 nm passes through the ultraviolet lens 26 by the band-pass filter 25 having a transmission peak wavelength of 300 nm and a half-width of 5 nm. The ultraviolet light passing through the ultraviolet lens 26 is branched in two directions of direct advance and reflection again by the half mirror 24b. only the specific wavelength component is extracted from the ultraviolet light passing through the half mirror 24b by the band-pass filter 25 and is picked up by the ultraviolet CCD camera 27. The image picked up by the ultraviolet CCD camera 27 is sent to the image processing apparatus 29.

Figure 13A:
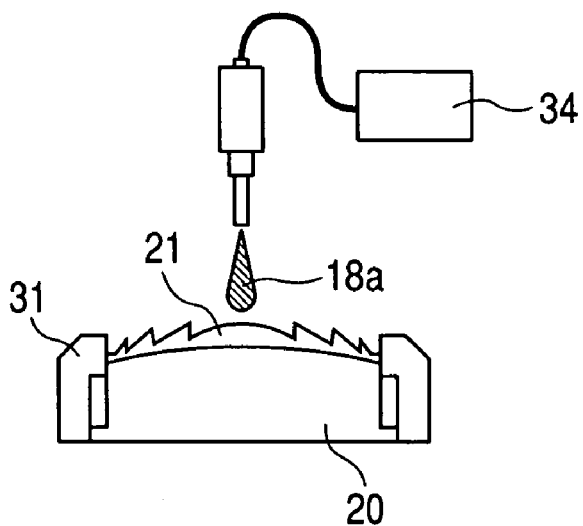
FIGS. 13A, 13B, 13C, 13D and 13E are schematic views showing the replica forming process of a diffractive optical device in the Embodiment 5.

Then, a measuring method making use of an ultraviolet-curable-resin cured-state measuring apparatus is described below by referring to FIGS. 13A to 13E. FIG. 13A is a schematic sectional view of a portion nearby an outer periphery of a molding die for molding a diffraction grating. A step of molding a miniature-shape diffraction optical device by using the molding die is described below. In FIG. 13A, an ultraviolet curable resin 18a whose absorbance greatly changes at an ultraviolet wavelength of 350 nm is dripped onto the center of a molding die 20 held by a molded-item support 31 in a quantity controlled by a dispenser 34. A miniature shape 21 is formed on the surface of the molding die 20.

Figure 13B:
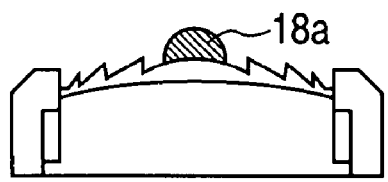

Then, FIG. 13B shows a state in which a very small quantity of the ultraviolet curable resin 18a is dripped on the center of the surface of the miniature shape 21.

Figure 13C:
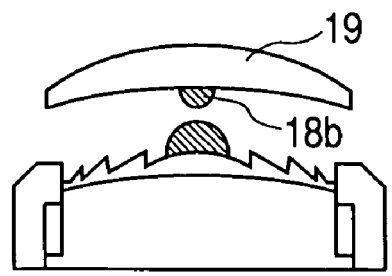

Then, in the step shown in FIG. 13C, a very small quantity of an ultraviolet curable resin 18b same as the ultraviolet curable resin 18a is dripped onto the center of a glass base material 19 serving as the substrate of a molded item to first bring the ultraviolet curable resin 18a on the glass base material 19 into contact with the ultraviolet curable resin 18b on the miniature shape 21. Then, the glass base material 19 is slowly lowered and fixed at a desired film-thickness position. The ultraviolet curable resin 18a and ultraviolet curable resin 18b (hereafter referred to as ultraviolet curable resin 18) are spread by means of the glass base material 19 and become a diffraction optical device filling a space surrounded by the miniature shape 21 and the glass base material 19.

Figure 13D:
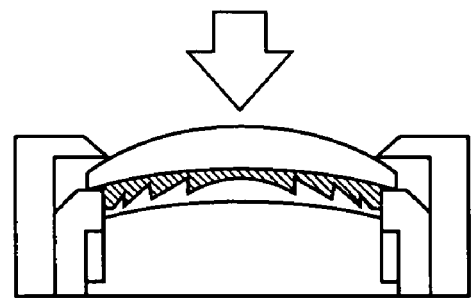

Then, in the step shown in FIG. 13D, the ultraviolet curable resin 18 is partially cured and then permanently cured by applying ultraviolet light (arrow) from the glass base material 19 side. In this case, the cured state of the ultraviolet curable resin is evaluated by using the cured-state measuring apparatus shown in FIG. 12. The ultraviolet light for the measurement also serves as the ultraviolet light used to cure the ultraviolet curable resin 18. At the time, it is possible to capture the in-face information on the cured state of the resin by extracting the ultraviolet light reflected from a measuring object by the band-pass filter 25 having a transmission peak wavelength of 350 nm and a half-width of 5 nm and taking in the ultraviolet light as an image by the ultraviolet CCD camera 27 and then transferring the image to the image processing apparatus 29. In this case, the light source for curing the resin and the light source for measuring absorbance are the same ultraviolet light source 23 and the ultraviolet light having the above spectrum shown in FIG. 7 in wavelengths of 250 to 400 nm is emitted from the light source.

Figure 13E:
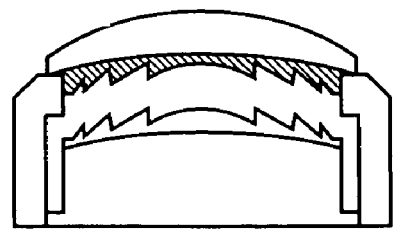

Then, in the step shown in FIG. 13E, the molded product is released from the die by raising the support 31 around the glass base material. The above steps are also executed for another die for forming a diffraction grating. Thus, two types of diffraction lenses respectively having a concave or convex shape at the circumference are completed.

According to this embodiment, by capturing a temporal change of the cured state of a resin following irradiation of ultraviolet light by the cured-state measuring apparatus shown in FIG. 12, it is possible to obtain the information on the dependency on a curing speed or curing time of an ultraviolet curable resin. Therefore, it is possible to determine optimum curing conditions and accurately control the cured state of an ultraviolet curable resin in the diffraction optical device fabrication process. Moreover, because of using ultraviolet light, it is possible to measure the cured state through a lens.

Embodiment 6

Figure 14:
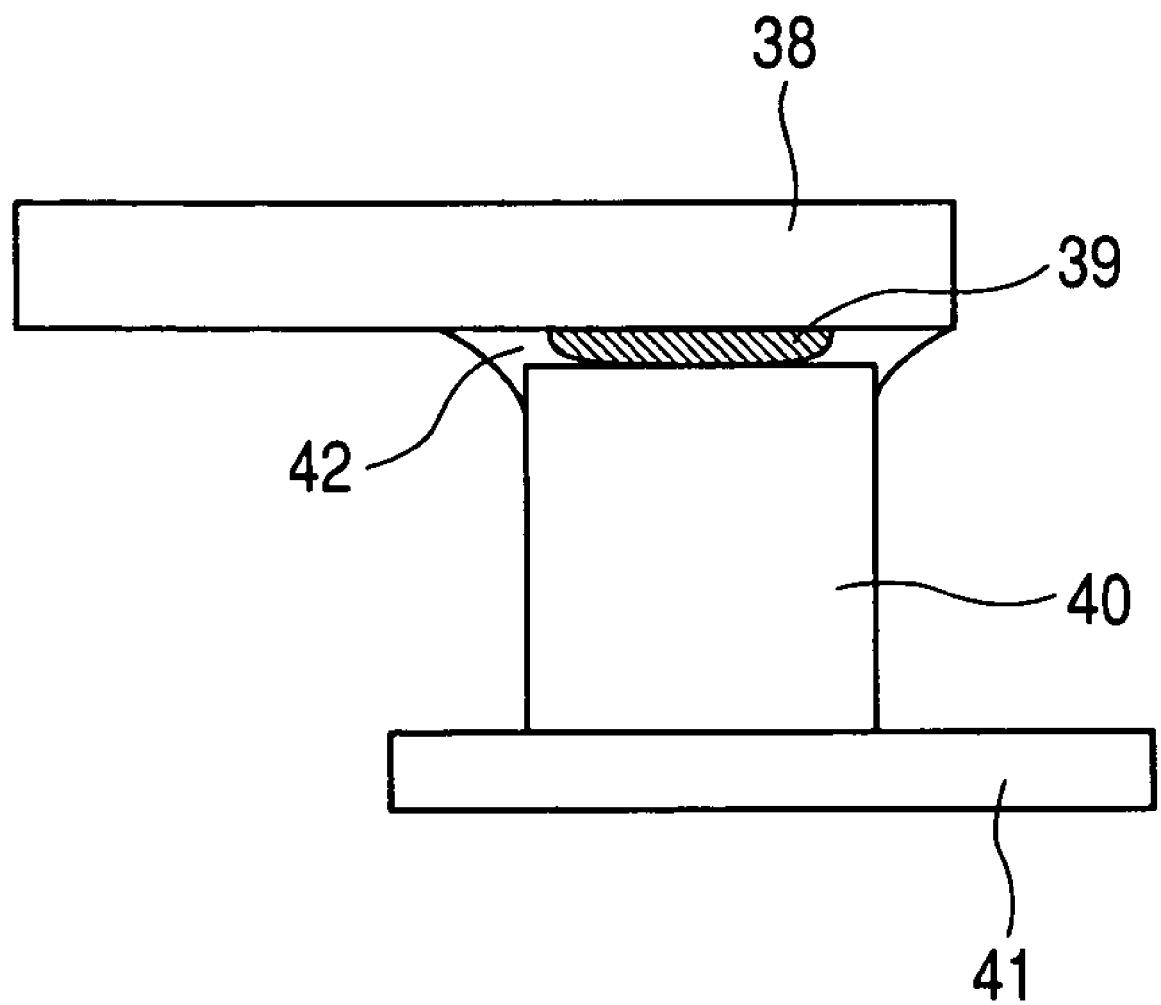
FIG. 14 is a schematic view of a compact-camera module in Embodiment 6.

FIG. 14 is a schematic view of a compact camera module used in Embodiment 6 of the present invention, in which a reaction curable resin is used for the compact camera module. The resin used is an epoxy adhesive (trade name ADEKA OPTOMER made by ASAHI DENKA KOGYO K.K.). When the resin is cured by irradiating ultraviolet light from the glass face side, the cured state of the resin is monitored by the cured-state measuring apparatus shown in FIG. 6 which is used in Embodiment 2. In FIG. 14, reference numeral 38 denotes a glass base material, 39 denotes an adhesive, 40 denotes a spacer, 41 denotes a Fresnel plate and 42 denotes a sealing material.

Embodiment 7

Figure 15:
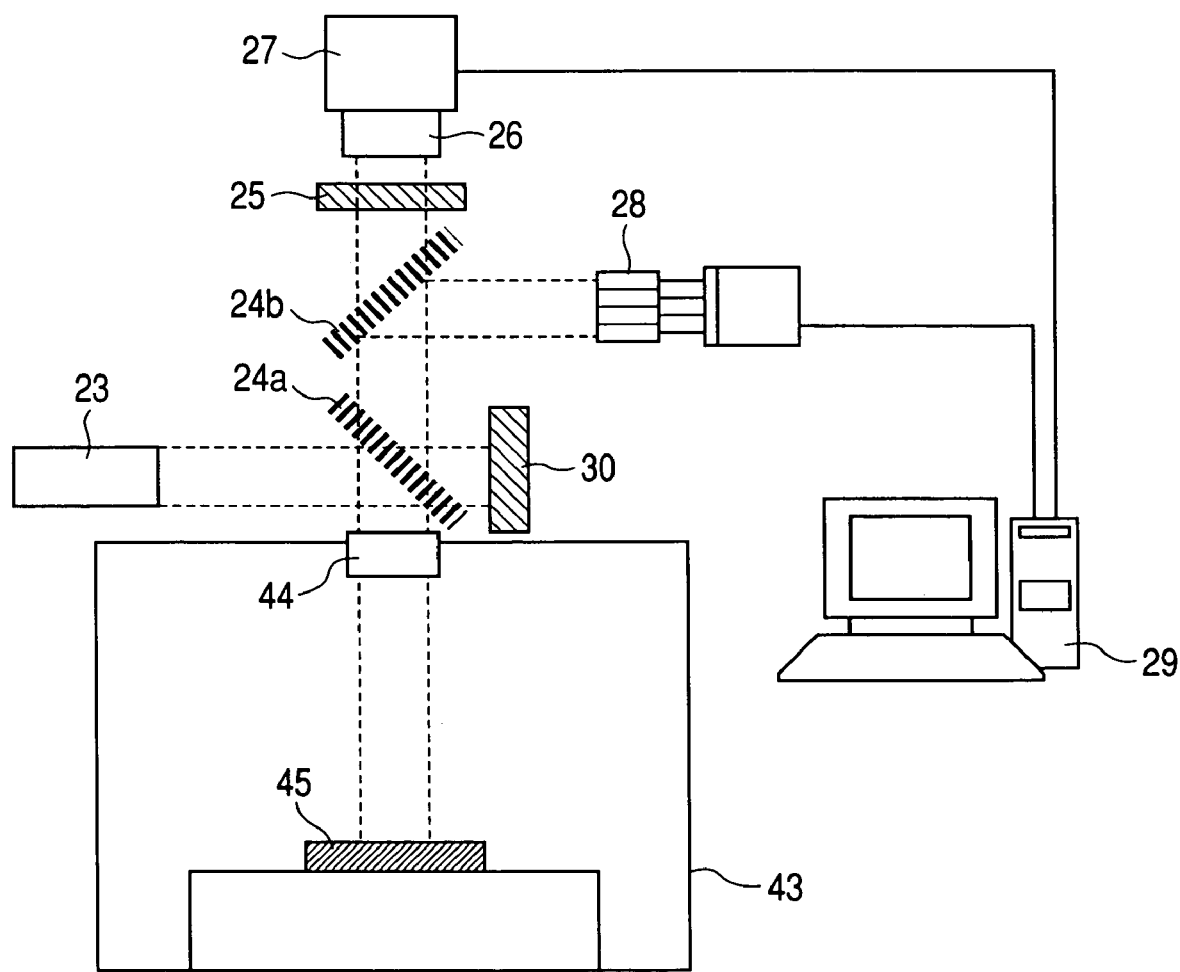
FIG. 15 is an image of a measurement conducted in Embodiment 7.

FIG. 15 shows Embodiment 7 of the present invention, in which a resin cured-state measuring method is used to measure the cured state of the resin in the annealing step of a DOE replica forming process. In FIG. 15, the same members as those in FIG. 12 are provided with the same reference numerals and their description is omitted. Reference numeral 43 denotes a high temperature furnace, 44 denotes a window member for monitoring the inside of a furnace and 45 denotes an ultraviolet curable resin serving as an object to be measured.

Figure 16:
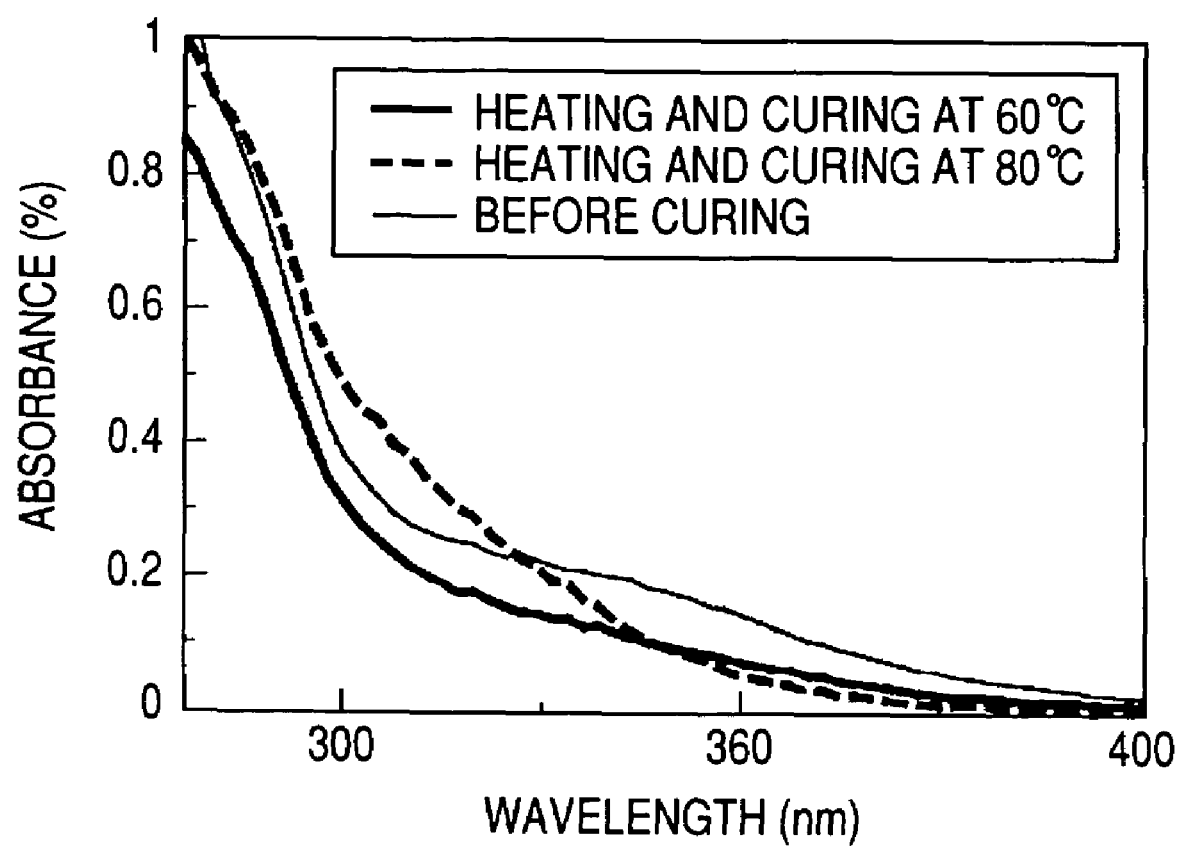
FIG. 16 is a plot with graphs showing the states of absorbance changes in annealing of ultraviolet curable resin C001 in Embodiment 7.

By using the above-described ultraviolet curable resin C001, the cured-state measurement shown in the embodiment 2 is executed to measure the changes in the cured state in the annealing step of a resin cured by ultraviolet light. In the annealing step, the ultraviolet curable resin 45 is put in the high temperature furnace 43 set to a temperature of 60 to 80° C. to heat it for 0 to 24 hours. The curing reaction of the ultraviolet curable resin 45 is measured while annealing. When C001 used as the ultraviolet curable resin 45 is annealed for 20 hours at 60° C. and 80° C., absorbances change as shown in FIG. 16. By capturing a change in the absorbance of the ultraviolet curable resin 45 in the high temperature furnace 43 by a cured-state measuring apparatus and monitoring the cured state through a window member 44 for monitoring the inside of a furnace, it is possible to control curing conditions, such as the annealing temperature and annealing time, and improve the yield.

In the present invention, it is easy to select an optical system, such as a lens or mirror, by using the ultraviolet light having wavelengths of 250 to 380 nm as measurement light. Moreover, even in a thermal environment, such as a furnace, the ultraviolet light is very useful, because it is possible to separate material information from heat information.

Moreover, an ultraviolet light source has an intensity not only for the ultraviolet light having a wavelength of 250 to 380 nm, but also for a visible light region. Therefore, by measuring an image in a visible light region at the same time, it is possible to capture an appearance (quality) and a cured state (performance) at the same time.

Furthermore, this method can be used not only for the replica forming process of a diffraction optical device, but also for various steps, such as formation, bonding and sealing by an ultraviolet curable resin.

Furthermore, when an object to be measured including a resin material is irradiated with measurement light and the light passing through the resin is captured by a CCD, it is possible to correlate the information to various processes for curing a resin, such as light irradiation or heating, by using the transmission type, incident-light type or reflection type as an illumination method.

A reaction-curable-resin cured-state measuring method of the present invention makes it possible to capture changes in the cured state of a reaction curable resin as a screen image and measure it as a function of time. Thereby, by confirming the cured state of a reaction curable resin, it is possible to analyze factors that cause curing irregularity and incomplete curing at the time curing is conducted and to derive optimum curing conditions. Therefore, it is possible to avoid a defective appearance due to the fluctuation of the cured state of a reaction curable resin and prevent a defective product due to chipping of a miniature shape portion when an optical device is released from a die or due to a remaining uncured portion caused by insufficient curing.

Moreover, because it is possible to measure a cured state by using ultraviolet light, it is possible to directly use a light source for curing when curing an ultraviolet curable resin. Therefore, it is possible to make a measuring apparatus compact and, particularly, to provide a measuring apparatus suitable for measurement in various in-line processes for UV curing printing and coating material curing. Moreover, it is possible to perform ultraviolet curing and cured-state measurement at the same time.

This application claims priority from Japanese Patent Application Nos. 2003-430423, filed on Dec. 25, 2003, and 2004-334804, filed on Nov. 18, 2004, which are hereby incorporated by reference.

What is claimed is:

1. A reaction-curable resin cured-state measuring method comprising:

a step of irradiating a reaction-curable resin, serving as an object to be measured, with ultraviolet light of at least one wavelength in a range from 250 to 380 nm, branching the ultraviolet light reflected from or transmitted through the reaction-curable resin in two directions, detecting a luminance value of one-hand branched ultraviolet light as screen image data having a certain area and detecting a spectral characteristic at one specific point of the other-hand branched ultraviolet light while the reaction-curable resin is curing;

a step of obtaining absorbances of the reaction-curable-resin at the one specific point from the spectral characteristic;

a step of obtaining a reaction rate at the one specific point from the absorbances;

a step of correlating the luminance value at the one specific point with the reaction rate; and a step of quantifying a progressing state of the curing reaction of the reaction-curable resin over an entire curing time as a screen image by comparing the luminance value as the screen image data and the reaction rate at the one specific point.

2. The method according to claim 1, further comprising a step of displaying a quantified screen image for a change rate corresponding to the reaction rate by setting a change of the reaction rate to 0% before the curing reaction and to 100% after completion of the curing reaction, and changing colors at a plurality of gradations.

3. The method according to claim 1, wherein the reaction-curable-resin is an ultraviolet-curable resin and the ultraviolet-curable resin is cured by the ultraviolet light.

4. The method according to claim 1, wherein the reaction-curable resin is an ultraviolet-curable resin for forming an optical device via replica molding.

5. A reaction-curable resin cured-state measuring apparatus comprising:

an ultraviolet light source for irradiating a reaction-curable resin, serving as an object to be measured, with ultraviolet light;

a half-mirror for branching the ultraviolet light reflected from or transmitted through the reaction-curable resin in two directions;

detection means for detecting a luminance value of one-hand ultraviolet light branched by the half-mirror as screen image data having a certain area;

an ultraviolet spectroscope for detecting a spectral characteristic at one specific point of the other-hand ultraviolet light branched by the half-mirror; and an image processing apparatus for obtaining absorbances of the reaction-curable resin at the one specific point from the spectral characteristic, obtaining a reaction rate at the one specific point from the absorbances, correlating the luminance value at the one specific point with the reaction rate and quantifying a progressing state of the curing reaction of the reaction-curable resin over an entire curing time as a screen image by comparing the luminance value as the screen image data and the reaction rate at the one specific point.

6. The apparatus according to claim 5, further comprising a band-pass filter for extracting only a light having a specific wavelength from the reflected or transmitted ultraviolet light, wherein the band-pass filter is set between the reaction-curable resin and the detection means.

7. The apparatus according to claim 6, wherein the detection means detects the luminance value of the reflected or transmitted ultraviolet light, and the light having a specific wavelength extracted by the band-pass filter has at least one wavelength in a range from 250 to 380 nm at which a maximum change of luminance values following curing of the reaction-curable resin appears.

8. The apparatus according to claim 7, wherein the image-processing apparatus displays a quantified screen image for a change rate corresponding to the reaction rate by setting a change in the reaction rate to 0% before the curing reaction and to 100% after completion of the curing reaction, and changing colors at a plurality of gradations.

* * * * *

UNITED STATES PATENT AND TRADEMARK OFFICE
CERTIFICATE OF CORRECTION

PATENT NO. : 7,323,693 B2
APPLICATION NO. : 11/013536
DATED : January 29, 2008
INVENTOR(S) : Tatsushi Sanuki et al.

It is certified that error appears in the above-identified patent and that said Letters Patent is hereby corrected as shown below:

<u>COLUMN 1</u>:

Line 26, "method," should read --method--.

<u>COLUMN 2</u>:

Line 15, "device-" should read --device--;
Line 37, "cured- state" should read --cured-state--; and
Line 59, "of" (second occurrence) should read --by--.

<u>COLUMN 3</u>:

Line 53, "setting." should read --setting--.

<u>COLUMN 4</u>:

Line 25, "apparatus" should read --apparatus in--; and
Line 30, "an" should read --a--.

<u>COLUMN 5</u>:

Line 35, "progresses" should read --progressed-- and
"only" should read --Only--.

<u>COLUMN 7</u>:

Line 18, "C0001has" should read --C0001 has--.

<u>COLUMN 9</u>:

Line 36, "intensity Io" should read --intensity $I_0$--.

<u>COLUMN 10</u>:

Line 66, "of." should read --of--.

UNITED STATES PATENT AND TRADEMARK OFFICE
CERTIFICATE OF CORRECTION

PATENT NO. : 7,323,693 B2
APPLICATION NO. : 11/013536
DATED : January 29, 2008
INVENTOR(S) : Tatsushi Sanuki et al.

It is certified that error appears in the above-identified patent and that said Letters Patent is hereby corrected as shown below:

COLUMN 11:

Line 1, "ultraviolet CCD" should read --ultraviolet CCD camera--.

COLUMN 12:

Line 29, "only" should read --Only--.

COLUMN 14:

Line 31, "CCD," should read --CCD camera,--.

Signed and Sealed this

Nineteenth Day of August, 2008

JON W. DUDAS
*Director of the United States Patent and Trademark Office*